Figure 1:
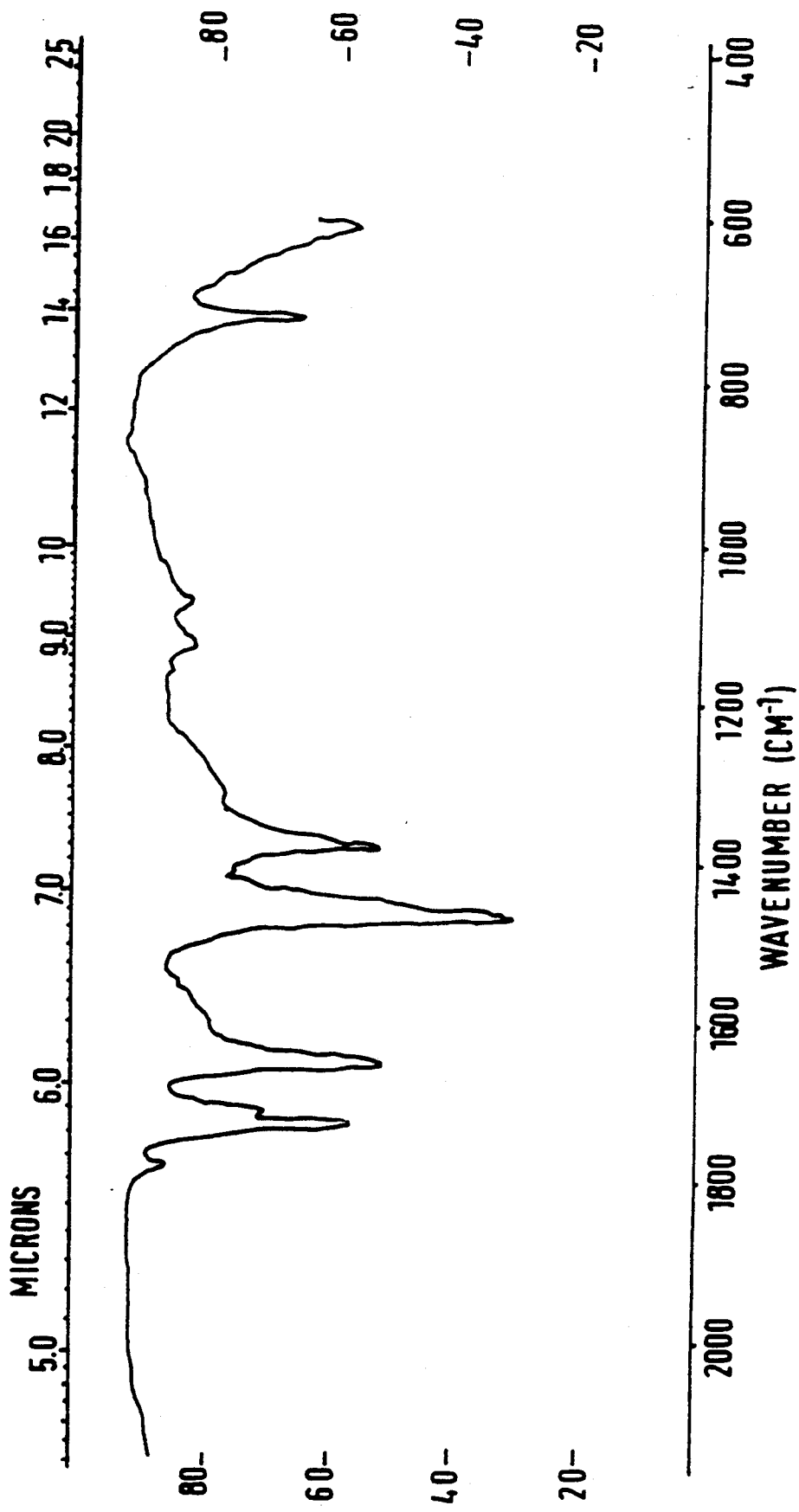

United States Patent [19]

Lewtas et al.

[11] Patent Number: 5,425,789
[45] Date of Patent: Jun. 20, 1995

[54] CHEMICAL COMPOSITIONS AND THEIR USE AS FUEL ADDITIVES

[75] Inventors: Kenneth Lewtas, Wantage; Edwin W. Lehmann, Faringdon; David P. Gillingham; John E. Maddox, both of Swindon, all of United Kingdom

[73] Assignee: Exxon Chemical Patents Inc., Linden, N.J.

[21] Appl. No.: 54,356

[22] Filed: Apr. 28, 1993

Related U.S. Application Data

[60] Division of Ser. No. 867,850, Apr. 13, 1992, abandoned, which is a continuation of Ser. No. 673,842, Mar. 19, 1991, abandoned, which is a continuation of Ser. No. 366,155, Jun. 14, 1989, abandoned, which is a continuation-in-part of Ser. No. 281,939, Dec. 6, 1988, abandoned, which is a continuation of Ser. No. 136,726, Dec. 22, 1987, abandoned.

[30] Foreign Application Priority Data

Dec. 22, 1986 [GB] United Kingdom ............. 8630594

[51] Int. Cl.⁶ .................................................. C10L 1/22
[52] U.S. Cl. .................................... 44/391; 44/399; 44/418
[58] Field of Search ................ 44/391, 399, 418, 370, 44/371, 372, 374

[56] References Cited

U.S. PATENT DOCUMENTS

| | | | |
|---|---|---|---|
| 2,542,542 | 2/1951 | Lippincott et al. | 252/56 |
| 2,657,984 | 11/1953 | Braithwaite, Jr. et al. | 44/71 |
| 2,937,203 | 5/1960 | Fuller | 564/156 |
| 2,971,027 | 2/1961 | Hotten | 564/153 |
| 3,048,479 | 8/1962 | Ilnyckyj et al. | 44/62 |
| 3,231,607 | 1/1966 | Hotten | 260/518 |
| 3,252,771 | 5/1966 | Clough et al. | 44/62 |
| 3,312,620 | 4/1967 | Low et al. | 564/156 |
| 3,312,695 | 4/1967 | Mühle | 564/156 |
| 3,444,082 | 5/1969 | Kautsky | 252/51.5 |
| 3,637,805 | 1/1972 | Burkhardt et al. | 564/153 |
| 3,785,789 | 1/1974 | Honnen et al. | 44/71 |
| 3,846,481 | 11/1974 | Gaydasch | 44/71 |
| 3,950,419 | 4/1976 | Baumann et al. | 564/156 |
| 3,951,614 | 4/1976 | Honnen et al. | 44/63 |
| 3,961,916 | 6/1976 | Ilnyckyj et al. | 44/62 |
| 4,211,534 | 7/1980 | Feldman | 44/62 |
| 4,375,973 | 3/1983 | Rossi et al. | 44/62 |
| 4,402,708 | 9/1983 | Oswald | 44/66 |
| 4,481,013 | 11/1984 | Tack et al. | 44/74 |
| 4,491,455 | 1/1985 | Ishizaki et al. | 44/62 |
| 4,737,239 | 4/1988 | Bernheim et al. | 162/158 |
| 5,002,589 | 3/1991 | Baillargeon et al. | 44/399 |
| 5,039,306 | 8/1991 | Baillargeon et al. | 44/391 |
| 5,092,908 | 3/1992 | Feldman et al. | 44/418 |
| 5,102,427 | 4/1992 | Feldman et al. | 44/418 |

FOREIGN PATENT DOCUMENTS

0061895A2 10/1982 European Pat. Off. ......... C10L 1/1

(List continued on next page.)

OTHER PUBLICATIONS

Journal of Institute of Petroleum, "New Laboratory Test for Predicting Low-temperature Operability of Diesel Fuels" vol. 52, No. 510, Jun. 1966, pp. 173–185.
Chemical Abstracts, vol. 103, 1985, No. 178081k (month unknown).

(List continued on next page.)

*Primary Examiner*—Jerry D. Johnson
*Attorney, Agent, or Firm*—Vivienne T. White

[57] ABSTRACT

A compound of the general formula

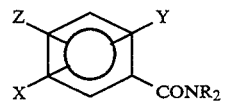

where
X is $CONR_2$ or $CO_2^-$ $^+H_2NR_2$
Y and Z are the same or different and selected from the group consisting of $CONR_2$, $CO_2R$, $OCOR$, —OR, —R, —NCOR and
one of Y or Z may be absent and
R is selected from the group consisting of alkyl, alkoxy alkyl or polyalkoxyalkyl preferably containing at least 10 carbon atoms in the main chain.

12 Claims, 2 Drawing Sheets

FOREIGN PATENT DOCUMENTS

| | | | |
|---|---|---|---|
| 0153176A2 | 8/1985 | European Pat. Off. | C10L 1/1 |
| 0153177A2 | 8/1985 | European Pat. Off. | C10L 1/1 |
| 2417788 | 10/1975 | Germany | 44/391 |
| 55-40640 | 10/1980 | Japan . | |
| 56-54037 | 12/1981 | Japan . | |
| 56-54038 | 12/1981 | Japan . | |
| 1263152B | 2/1972 | United Kingdom | C10L 1/1 |
| 1396941 | 6/1975 | United Kingdom | A01N 9/1 |
| 1442143 | 7/1976 | United Kingdom | C01L 1/18 |
| 1445580 | 8/1976 | United Kingdom . | |
| 1468588 | 3/1977 | United Kingdom | C01L 1/1 |
| 1469016 | 3/1977 | United Kingdom | C10L 1/1 |
| 2023645B | 10/1982 | United Kingdom | C01L 1/1 |
| 2129012A | 10/1983 | United Kingdom . | |

OTHER PUBLICATIONS

Chemical Abstracts, vol. 91, 1979, No. 194449a (month unknown).

Chemical Abstracts, vol. 78, 1973, No. 42992r (month unknown).

Chemical Abstracts, vol. 75, 1971, No. 5913h (month unknown).

Journal of Organic Chemistry, vol. 24, 1959, pp. 26–28, Easton, U.S.; E. A. Lawton: "*Synthesis of pyromellitonitrile and related compounds*" pp. 27–28: experimental *(month unknown)*.

Synthesis, 1972, pp. 634–635, Stuttgart, DE; H. Schindlbauer et al.: "*Amidierung MIT Hexamethylphosphorsauretriamid*", p. 635, Table (month unknown).

Monatshefte Fur Chemie, vol. 100, 1969, pp. 1583–1589, Wien, AT; H. Schinlbauer: "*Reaktionen mit Dimethylformamid, 2.MITT.: Uber die Bildung von Carbonsauredimethylamiden*" *p. 1588 (month unknown)*.

CHEMICAL COMPOSITIONS AND THEIR USE AS FUEL ADDITIVES

This is a division of application Ser. No. 867,850, filed Apr. 13, 1992 now abandoned, which is a continuation of U.S. Ser. No. 673,842, filed Mar. 19, 1991, now abandoned which is a continuation of U.S. Ser. No. 366,155, f. Jun. 14, 1989, now abandoned which is a continuation in part of U.S. Ser. No. 281,939, f. Dec. 6, 1988, now abandoned, which is a continuation of U.S. Ser. 136,726, f. Dec. 22, 1987, now abandoned.

This invention relates to new chemical compounds which are useful as crystal modifiers in liquid hydrocarbons particularly fuels especially distillate fuels, the use of these chemicals as distillate fuel additives and to fuels containing the additives.

Long n-alkyl derivatives of difunctional compounds have previously been described as has their use as wax crystal modifiers, to wit derivatives of alkenyl succinic acid (U.S. Pat. No. 3,444,082), maleic acid (U.S. Pat. No. 4,211,534) and phthalic acid (GB 2923645, U.S. Pat. Nos. 4,375,973 and 4,402,708.

We have now found that certain novel compounds are useful as wax crystal modifiers in distillate fuels making possible a significant reduction in the size of the wax crystals formed to below 4000 nanometres sometimes below 2000 nanometres preferably below 1000 nanometres when the modifiers are used alone or in combination with other known wax crystal modifiers.

The present invention therefore provides a compound of the general formula

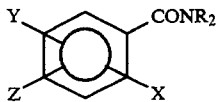

where
X is $CONR_2$ or $CO_2^- {}^+H_2NR_2$
Y and Z are the same or different and selected from the group consisting of $CONR_2$, $CO_2R$, $OCOR$, —OR, —R, —NCOR and
one of Y or Z may be absent and
R is selected from the group consisting of alkyl, alkoxy alkyl or polyalkoxyalkyl preferably containing at least 10 carbon atoms in the main chain.

The compounds of the present invention may be prepared by reacting pyromellitic dianhydride with amines, alcohols, quaternary ammonium salts etc. Where the compounds are the amides or amine salts they are preferably of a secondary amine which has a hydrogen- and carbon-containing group containing at least 10 carbon atoms. Such amides or salts may be prepared by reacting the acid or anhydride with a secondary amine or alternatively by reacting an amine derivative with a carboxylic acid or anhydride thereof. Removal of water and heating are generally necessary to prepare the amides from the acids. Alternatively the carboxylic acid may be reacted with an alcohol containing at least 10 carbon atoms or a mixture of an alcohol and an amine.

When the compounds are used as fuel additives we prefer that R, contains 10 to 30 preferable 10 to 22 carbon atoms, for example 14 to 20 carbon atoms and are preferably straight chain or branched at the 1 or 2 position. The other hydrogen- and carbon-containing groups can be shorter e.g. less than 6 carbon atoms or may if desired have at least 10 carbon atoms. Suitable alkyl groups include methyl, ethyl, propyl, hexyl, decyl, dodecyl, tetradecyl, eicosyl and docosyl (behenyl).

These compounds are especially useful as fuel additives especially for mineral oils containing paraffin wax which have the characteristic of becoming less fluid as the temperature of the oil decreases. This loss of fluidity is due to the crystallisation of the wax into plate-like crystals which eventually form a spongy mass entrapping the oil therein. The temperature at which the wax crystals begin to form being known as the Cloud Point and the temperature at which the wax prevents the oil from pouring is the Pour Point.

It has long been known that various additives act as wax crystal modifiers when blended with waxy mineral oils. These compositions modify the size and shape of wax crystals and reduce the cohesive forces between the crystals and between the wax and the oil in such a manner as to permit the oil to remain fluid at lower temperature Various Pour Point depressants have been described in the literature and several of these are in commercial use. For example, U.S. Pat. No. 3,048,479 teaches the use of copolymers of ethylene and $C_1$–$C_5$ vinyl esters, e.g. vinyl acetate, as pour depressants for fuels, specifically heating oils, diesel and jet fuels. Hydrocarbon polymeric pour depressants based on ethylene and higher alpha-olefins, e.g. propylene, are also known.

U.S. Pat. No. 3,961,916 teaches the use of a mixture of copolymers, to control the size of the wax crystals and United Kingdom Patent 1,263,152 suggests that the size c the wax crystals may be controlled by using a copolymer having a low degree of side chain branching. Both systems improve the ability of the fuel to pass through filters as determined by the Cold Filter Plugging Point (CFPP) test since instead of plate like crystals formed without the presence of additives the needle shaped wax crystals produced will not block the pores of the filter rather forming a porous cake on the filter allowing passage of the remaining fluid.

Other additives have also been proposed for example, United Kingdom Patent 1,469,016, suggest that the copolymers of di-n-alkyl fumarates and vinyl acetate which have previously been used as pour depressant for lubricating oils may be used as co-additives with ethylene/vinyl acetate copolymers in the treatment of distillate fuels with high final boiling points to improve their low temperature flow properties.

U.S. Pat. No. 3,252,771 relates to the use of polymers of $C_{16}$ to $C_{18}$ alpha-olefins obtained by polymerising olefin mixtures that predominate in normal $C_{16}$ to $C_{18}$ alpha-olefins with aluminium trichloride/alkyl halide catalysts as pour depressants in distillate fuels of the broad boiling, easy-to-treat types available in the United States in the early 1960's.

It has also been proposed to use additives based on olefin/maleic anhydride copolymers. For example, U.S. Pat. No. 2,542,542 uses copolymers of olefins such as octadecene with maleic anhydride esterified with an alcohol such as lauryl alcohol as pour depressants and United Kingdom Patent 1,468,588 uses copolymers of $C_{22}$–$C_{28}$ olefins with maleic anhydride esterified with behenyl alcohol as co-additives for distillate fuels.

Similarly, Japanese Patent Publication 5,654,037 uses olefin/maleic anhydride copolymers which have been reacted with amines as pour point depressants and in Japanese Patent Publication 5,654,033 the derivatives of the olefin/maleic anhydride copolymers are used together with conventional middle distillate flow improvers such as ethylene vinyl acetate copolymers.

Japanese Patent Publication 5,540,640 discloses the use of olefin/maleic anhydride copolymers (not esterified) and states that the olefins used should contain more than 20 carbon atoms to obtain CFPP activity.

United Kingdom 2,192,012 uses mixtures of esterified olefin/maleic anhydride copolymers and low molecular weight polyethylene, the esterified copolymers being ineffective when used as sole additives. The patent specifies that the olefin should contain 10–30 carbon atoms and the alcohol 6–28 carbon atoms with the longest chain in the alcohol containing 22–40 carbon atoms.

U.S. Pat. Nos. 3,444,082; 4,211,534; 4,375,973 and 4,402,708 discussed previously suggest the use of certain nitrogen containing compounds.

The improvement in CFPP activity achieved by the incorporation of the additives of these Patents is achieved by modifying the size and shape of the wax crystals forming to produce needle like crystals generally of particle size 10 microns or bigger typically 30 to 100 microns. In operation of diesel engines or heating systems at low temperatures, these crystals do not generally pass through the filters but form a permeable cake on the filter allowing the liquid fuel to pass, the wax crystals will subsequently dissolve as the engine and the fuel heats up, which can be by the bulk fuel being heated by recycled fuel. This can, however, result in the wax crystals blocking the filters, leading to starting problems and problems at the start of driving in cold weather or failure of fuel heating systems.

We have found that by using the compounds of the present invention particularly small wax crystals may be obtained which will pass through the filters of typical diesel engines and heating systems rather than forming a cake on the filter. We also find that the use enhances the formation of nodular crystals which are desirable for creating permeable wax filter cakes.

The amount of the compound added to the distillate fuel oil is preferably 0.001 to 0.5 wt. %, for example 0.01 to 0.10 wt. % based on the weight of fuel.

The compound may conveniently be dissolved in a suitable solvent to form a concentrate of from 20 to 90, e.g. 30 to 80 weight % in the solvent. Suitable solvents include kerosene, aromatic naphthas, mineral lubricating oils etc.

The use of the additives of this invention allows distillate fuel oil boiling in the range 120° C. to 500° C. and which has a wax content of at least 0.5 wt. % at a temperature of 10° C. below the wax appearance temperature, to be produced with wax crystals having an average particle size less than 4000 nanometres, sometimes less than 2000 nanometres and depending on the fuel, the crystals can be submicron size.

The Wax Appearance Temperature (WAT) of the fuel is measured by differential scanning calorimetry (DSC). In this test a small sample of fuel (25 ul) is cooled at 2°C./minute together with a reference sample of similar thermal capacity but which will not precipitate wax in the temperature range of interest (such as kerosene). An exotherm is observed when crystallisation commences in the sample. For example the WAT of the fuel may be measured by the extrapolation technique on the Mettle PA 20003.

The wax content is derived from the DSC trace by integrating the area enclosed by the baseline and the exotherm down to the specified temperature. The calibration having been previously performed on a known amount of crystallizing wax.

The wax crystal average particle size is measured by analysing a Scanning Electron Micrograph of a fuel sample at a magnification of 4000 to 8000× and measuring the longest axis of 50 crystals over a predetermined grid. We find that providing the average size is less than 4000 nanometres the wax will begin to pass through the typical paper filters used in diesel engines together with the fuel although we prefer that the size be below 3000 nanometres, more preferably below 2000 and most preferably below 1000 nanometres, the actual size attainable depends upon the original nature of the fuel and the nature and amount of additive used but we have found that these sizes and smaller are attainable.

The ability to obtain such small wax crystals in the fuel shows significant benefit in diesel engine operability as shown by pumping fuel that has been previously stirred (to remove settled wax effects) through a diesel filter at from 8 to 15 ml/second and 1.0 to 2.4 liters per minute per square metre of filter surface area at a temperature at least 5° C. below the wax appearance temperature with at least 1 wt. % of the fuel being present in the form of solid wax. Both fuel and wax are considered to successfully pass through the filter if one or more of the following criteria are satisfied:

(i) when 18 to 20 liters of fuel have passed through the filter the pressure drop across the filter does not exceed 50 KPa, preferably 25 KPa, more preferably 10 KPa, most preferably 5 KPa.

(ii) At least 60%, preferably at least 80%, more preferably at least 90 wt. % of the wax present in the fuel, as determined by the DSC test is found to be present in the fuel leaving the filter.

(iii) Whilst pumping 18 to 20 liters of fuel through the filter, the flow rate always remains at above 60% of the initial flow rate and preferably above 80%.

These fuels containing the compounds of this invention have outstanding benefits compared to previous distillate fuels improved in their cold flow properties by the addition of conventional additives. For example the fuels are operable at temperatures approaching the pour point and not restricted by the inability to pass the CFPP test. Hence these fuels either pass the CFPP test at significantly lower temperatures or obviate the need to pass that test. The fuels also have improved cold start performance at low temperatures since they do not rely on recirculation of warm fuel to dissolve undesirable wax deposits.

The best effect is usually obtained when the compounds of the invention are used in combination with other additives known for improving the cold flow properties of distillate fuels generally, although they may be used on their own.

The compounds are preferably used together with what are known as comb polymers which have the general formula

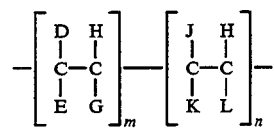

where
D=R, CO.OR, OCO.R, R'CO.OR or OR
E=H or CH$_3$ or D or R'

G=H, or D
m=1.0 (homopolymer) to 0.4 (mole ratio)
J=H, R', Aryl or Heterocyclic group, R'CO.OR
K=H, CO.OR', OCO.R', OR', CO$_2$H
L=H, R', CO.OR', OCO.R', Aryl, CO$_2$H
n=0.0 to 0.6 (mole ratio)
R≧C$_{10}$
R'≧C$_1$ Another monomer may be terpolymerized if necessary.

Examples of suitable comb polymers are the fumarate/vinyl acetate particularly those described in our European Patent applications 0153176, 0153177, 85301047 and 85301048 and esterified olefine/maleic anhydride copolymers and the polymers and copolymers of alpha olefines and esterified copolymers of styrene and maleic anhydride.

Examples of other additives with which the compounds of the present invention may be used are the polyoxyalkylene esters, ethers, ester/ethers and mixtures thereof, particularly those containing at least one, preferably at least two C$_{10}$ to C$_{30}$ linear saturated alkyl groups and a polyoxyalkylene glycol group of molecular weight 100 to 5,000 preferably 200 to 5,000, the alkyl group in said polyoxyalkylene glycol containing from 1 to 4 carbon atoms. These materials form the subject of European Patent Publication 0,061,895 A2. Other such additives are described in U.S. Pat. No. 4,491,455.

The preferred esters, ethers or ester/ethers which may be used may be structurally depicted by the formula:

R—O(A)—O—R'' where R and R'' are the same or different and may be

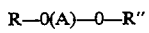 i)

 ii)

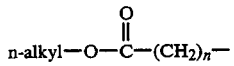 iii)

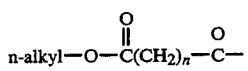 iv)

the alkyl group being linear and saturated and containing 10 to 30 carbon atoms, and A represents the polyoxyalkylene segment of the glycol in which the alkylene group has 1 to 4 carbon atoms, such as polyoxymethylene, polyoxyethylene or polyoxytrimethylene moiety which is substantially linear; some degree of branching with lower alkyl side chains (such as in polyoxypropylene glycol) may be tolerated but it is preferred the glycol should be substantially linear, A may also contain nitrogen.

Suitable glycols generally are the substantially linear polyethylene glycols (PEG) and polypropylene glycols (PPG) having a molecular weight of about 100 to 5,000, preferably about 200 to 2,000. Esters are preferred and fatty acids containing from 10 –30 carbon atoms are useful for reacting with the glycols to form the ester additives and it is preferred to use a C$_{18}$–C$_{24}$ fatty acid, especially behenic acids. The esters may also be prepared by esterifying polyethoxylated fatty acids or polyethoxylated alcohols.

Polyoxyalkylene diesters, diethers, ether/esters and mixtures thereof are suitable as additives with diesters preferred for use in narrow boiling distillates whilst minor amounts of monoethers and monoesters may also be present and are often formed in the manufacturing process. It is important for additive performance that a major amount of the dialkyl compound is present. In particular, stearic or behenic diesters of polyethylene glycol, polypropylene glycol or polyethylene/polypropylene glycol mixtures are preferred.

The compounds of this invention may also be used with ethylene unsaturated ester copolymer flow improvers. The unsaturated monomers which may be copolymerised with ethylene include unsaturated mono and diesters of the general formula:

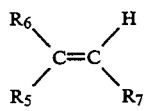

wherein R$_6$ is hydrogen or methyl, R$_5$ is a —OOR$_8$ group wherein R$_8$ is hydrogen formate or a C$_1$ to C$_{28}$, more usually C$_1$ to C$_{17}$, and preferably a C$_1$ to C$_8$, straight or branched chain alkyl group; or R$_5$ is a —COOR$_8$ group wherein R$_8$ is as previously described but is not hydrogen and R$_7$ is hydrogen or —COOR$_8$ as previously defined. The monomer, when R6 and R7 are hydrogen and R5 is —OOCR$_8$, includes vinyl alcohol esters of C$_1$ to C$_{29}$, more usually C$_1$ to C5, monocarboxylic acid, and preferably C$_2$ to C$_{29}$, more usually C$_1$ to C5 monocarboxylic acid, and preferably C$_2$ to C$_5$ monocarboxylic acid. Examples of vinyl esters which may be copolymerised with ethylene include vinyl acetate, vinyl propionate and vinyl butyrate or isobutyrate, vinyl acetate being preferred. We prefer that the copolymers contain from 5 to 40 wt. % of the vinyl ester, more preferably from 10 to 35 wt. % vinyl ester. They may also be mixtures of two copolymers such as those described in U.S. Pat No. 3,961,916. It is preferred that these copolymers have a number average molecular weight as measured by vapour phase osmometry of 1,000 to 10,000, preferably, 1,000 to 5,000.

The compounds of the invention may also be used in distillate fuels in combination with other polar compounds, either ionic or non-ionic, which have the capability in fuels of acting as wax crystal growth inhibitors. Polar nitrogen containing compounds have been found to be especially effective when used in combination with the glycol esters, ethers or ester/ethers and such three component mixtures are within the scope of the present invention. These polar compounds are generally amine salts and/or amides formed by reaction of at least one molar proportion of hydrocarbyl substituted amines with a molar proportion of hydrocarbyl acid having 1 to 4 carboxylic acid groups or their anhydrides; ester/amides may also be used containing 30 to 300, preferably 50 to 150 total carbon atoms. These nitrogen compounds are described in U.S. Pat. No. 4,211,534. Suitable amines are usually long chain C$_{12}$ –C$_{40}$ primary, secondary, tertiary or quaternary amines or mixtures thereof but shorter chain amines may be used provided the resulting nitrogen compound is oil soluble and therefore normally containing about 30 to 300 total carbon atoms. The nitrogen compound preferably contains at least one straight chain C$_8$ to C40, preferably C$_{14}$ to C$_{24}$ alkyl segment.

Suitable amines include primary, secondary, tertiary or quaternary, but preferably are secondary. Tertiary and quaternary amines can only form amine salts. Examples of amines include tetradecyl amine, cocoamine, hydrogenated tallow amine and the like. Examples of secondary amines include dioctacedyl amine, methylbehenyl amine and the like. Amine mixtures are also suitable and many amines derived from natural materials are mixtures. The preferred amine is a secondary hydrogenated tallow amine of the formula $HNR_1R_2$ where in $R_1$ and $R_2$ are alkyl groups derived from hydrogenated tallow fat composed of approximately 4% $C_{14}$, 31% $C_{16}$, 59% $C_{18}$.

Examples of suitable carboxylic acids and their anhydrides for preparing these nitrogen compounds include cyclohexane, 1,2 dicarboxylic acid, cyclohexene, 1,2-dicarboxylic acid, cyclopentane 1,2 dicarboxylic acid, naphthalene dicarboxylic acid and the like. Generally, these acids will have about 5–13 cabon atoms in the cyclic moiety. Preferred acids useful in the present invention are benzene dicarboxylic acids such as phthalic acid, isophthalic acid, and terephthalic acid. Phthalic acid or its anhydride is particularly preferred. The particularly preferred compound is the amide-amine salt formed by reacting 1 molar portion of phthalic anhydride with 2 molar portions of dihydrogenated tallow amine. Another preferred compound is the diamide formed by dehydrating this amide-amine salt.

Hydrocarbon polymers may also be used as part of the additive combination which may be represented with the following general formula:

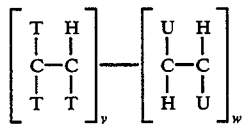

where
T = H or R'
U = H, T or Aryl
v = 1.0 to 0.0 (mole ratio)
w = 0.0 to 1.0 (mole ratio)
where $R^1$ is alkyl.

These polymers may be made directly from ethylenically unsaturated monomers or indirectly by hydrogenating the polymer made from monomers such as isoprene, butadiene etc.

A particularly preferred hydrocarbon polymer is a copolymer of ethylene and propylene having an ethylene content preferably between 20 and 60% (w/w) and is commonly made via homogenous catalysis.

The Additives of the present invention may also be used in combination with the sulpho carboxy materials described in our application U.S. Ser. No. 324,598 which claims use of compounds of the general formula:

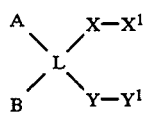

where

A and B may be the same or different and may be alkyl, alkenyl or aryl;
L is selected from the group consisting of
>CH—CH< and
>C=C< and
A, B and L together can constitute part of a cyclic structure which can be aromatic, alicyclic or mixed aromatic/alicyclic, and with the proviso that the groups —X—$X^1$ and Y—$Y^1$ are located on different carbon atoms constituting L and in that when A, B and L do not constitute part of a cyclic structure one of A or B may be hydrogen and in that when L is non-cyclic ethylenic, said X—$X^1$ and Y—$Y^1$ groupings are present in a cis configuration;
X is selected from the group consisting of
$SO_3^{(-)}$, —C(O)—, —C(O)O$^{(-)}$, —$R^4$—C(O)—, —$NR^3$C(O)—$R^4$O—, —$R^4$OC(O)—, —$R^4$— and —NC(O)—;
$X^1$ is selected from the group consisting of
$N^+R_3{}^3R^1$, $N^+HR_2{}^3R^1$, $H_2N^+R^3R^1$, $H_3N^+R^1$, —$NR^3R^1$, and $R^1$;
Y is —$SO_3^{(-)}$ or —$SO_2$;
when Y is $SO_3(-)$ $y^1$ is selected from the group consisting of $N^{(+)}R_2{}^3R^2$, $HN^{(+)}R_2{}^3R^2$, $H_2N^{(+)}R^3R^2$ and $H_3N^{(+)}R^2$
and when Y is —$SO_2$— yl is —$OR^2$, —$NR^3R^2$ or —$R^2$
and wherein $R^1$ and $R^2$ are independently selected from the group consisting of alkyl alkoxy alkyl or polyalkoxyalkyl groups containing at least 10 carbon atoms in their chain;
$R^3$ is hydrocarbyl and each $R^3$ may be same or different; and
$R^4$ is —$(CH_2)_n$ where n is from 0 to 5.

Multicomponent additive systems may be used and the ratios of additives to be used will depend on the fuel to be treated.

The additive systems which form part of the present invention may conveniently be supplied as concentrates for incorporation into the bulk distillate fuel. These concentrates may also contain other additives as required. These concentrates preferably contain from 3 to 75 wt. %, more preferably 3 to 60 wt. %, most preferably 10 to 50 wt. % of the additives preferably in solution in oil. Such concentrates are also within the scope of the present invention. The additives of this invention may be used in the broad range of distillate fuels boiling in the range 120° to 500° C.

The invention is illustrated by the following Examples.

PREPARATION

Example 1

Additive X

The 1,2,4,5 tetra, N,N di(hydrogenated tallow) amido benzene was prepared by reacting 4 moles of dihydrogenated tallow amine with one mole of pyromellitic dianhydride in the melt at 225° C. in a flask containing a stirrer, temperature probes, Nitrogen pruge and distillation condenser. Water was distilled out for approximately 8 hours and the product obtained.

Figure 2:
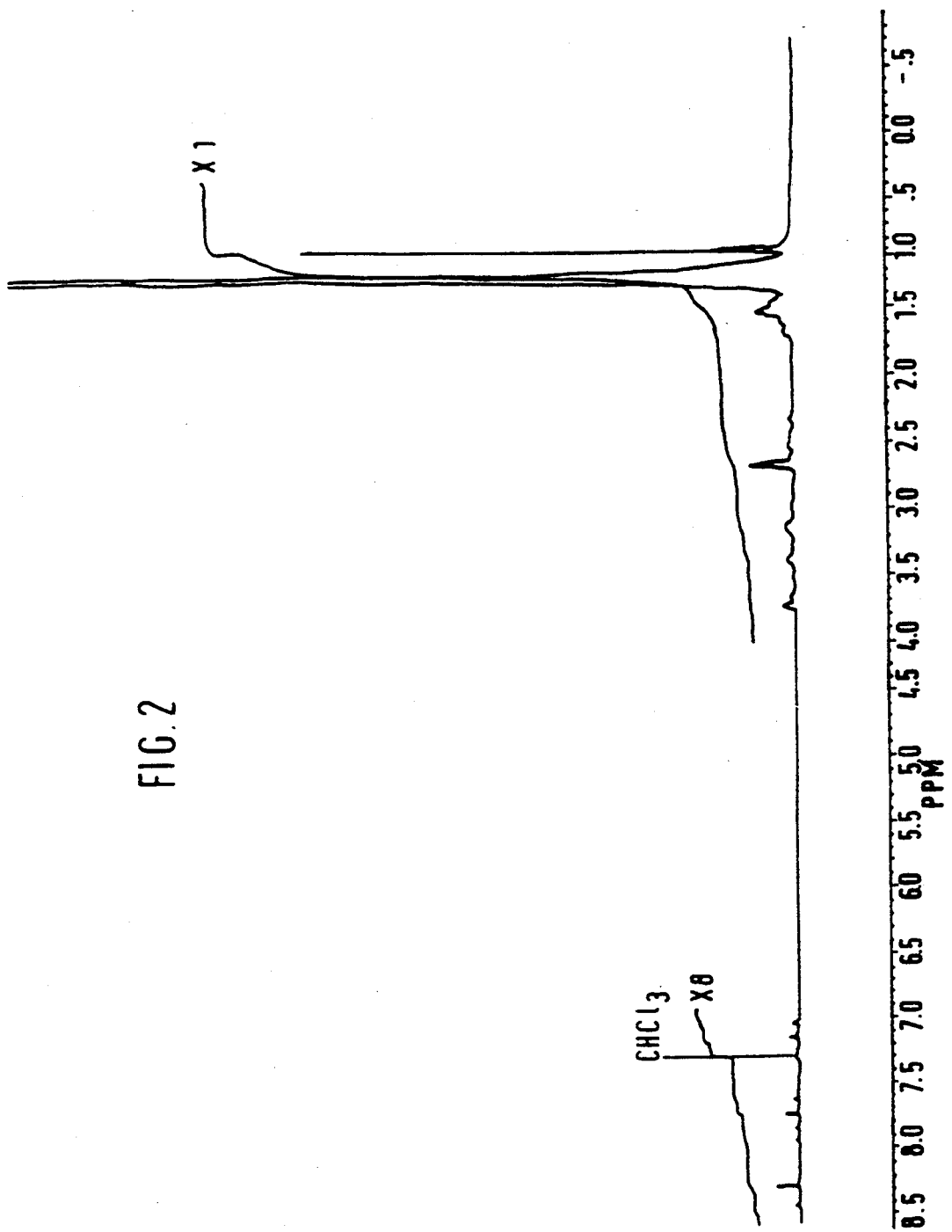

The product was analysed by Infra Red and 500 MHz Nuclear Magnetic Resonance Spectroscopy and the spectra which is attached hereto as FIGS. 1 and 2 confirmed the structure to be a mixture of the tetraamide, triamide/mono salt and diamide/disalt in the following ratios: 44: 37: 19 respectively.

Additive Y

The pyromellitic dianhydride (1 mole) was reacted with 2 moles of Alfol 2022 a mixture of n-alkyl alcohols (n $C_{18}$ 7% max, n $C_{20}$ 58% min, n $C_{22}$ 30% min and n $C_{24}$ 6% max), at 120° C. for 2 hours in the absence of any solvent. 2 moles of dihydrogenated tallow amine was then added to the reaction mixture, the temperature elevated to 150° C. and the reaction continued for another 2 hours. The final product having 2 functional groups esterified and the other 2 aminated (i.e. in the form of amide or carboxylate/dialkyl ammonium salt).

Testing

The effectiveness of the product of Example 1 in additive systems to improvers filterability of distillate fuels were determined by the following methods.

The flow improver Extended Programmed Cooling Test (XPCT) which is a slow cooling test designed to indicate whether the wax in the fuel will pass through filters such as are found in heating oil distribution system.

In the test, the cold flow properties of the described fuels containing the additives were determined as follows. 300 ml. of fuel are cooled linearly at 1° C./hour to the test temperature and the temperature ther held constant. After 2 hours at −9° C., approximately 20 ml. of the surface layer is removed as the abnormally large wax crystals which tend to form on the oil/air interface during cooling. Wax which has settled in the bottle is dispersed by gentle stirring, then a Cold Filter Plugging Point CFPP filter assembly which is described in detail in "Journal of the Institute of Petroleum", Volume 52, Number 510, Jun. 1966, pp. 173-285 is inserted. The tap is opened to apply a vacuum of 500 mm. of mercury and closed when 200 ml. of fuel have passed through the filter into the graduated receiver. A PASS is recorded if the 200 ml, will pass through a given mesh size or a FAIL if the filter has become blocked.

A series of CFPP filter assemblies with filter screens of 10 um to 45 um including LTFT (AMS 100.65) and a Volzwagen Tank filter (part no. KA/4-270/65.431-201-511) both intermediate between 30 and 40 um are used to determine the finest mesh the fuel will pass.

Wax settling studies were also performed prior to PCT filtration. The extent of the setled layer was visually measured as a % of the total fuel volume. Thus extensive wax settling would be given by a low number whilst an unsettled fluid fuel would be at a state of 100%. Care must be taken because poor samples of gelled fuel with large wax crystals almost always exhibit high values, therefore these results should be recorded as "gel".

The following additives were used
i) Additive A

A1 was a mixture of two ethylene-vinyl acetate copolymers, 3 parts by weight of one consisting of ethylene and about 36 wt. % vinyl acetate, and has a number average molecular weight of about 1800 (VPO) and one part by weight of A2.

A2 consists of a polymer containing 13.5 wt. % vinyl acetate and has a number average molecular weight of 3500 (VPO).

(ii) Additive B

A copolymer of ethylene and propylene containing 56 wt. % ethylene and of number average molecular weight of 50,000.

(iii) Additive C

D was made esterifying a 1:1 molar styrene-maleic anhydride copolymer with 2 moles of $C_{14}H_{29}OH$ per mole of anhydride groups were used in the esterification (slight excess, 5% alcohol used) step using p-toluene sulphonic acid as the catalyst (1/10 mole) in xylene solvent, which gave a molecular weight (Mn) of 50,000 and contained 3% (w/w) unreacted alcohol.

(iv) Additive D

N N dihydrogenated tallow ammonium salt of 2N $N^1$ dihydrogenated tallow benzene sulphonate.

(v) Additive E

E was made by polymerizing a 1:1 (molar) mixture of styrene and di-n-tetradecyl fumarate in cycohexane under the following conditions. Di-T-butyl peroctate was used as an initiator, 20% of the styrene was charged initially with all of the fumarate and the remaining 80% of the styrene was charged over one hour. After this time a soak period of fifteen minutes was used. The pressure was maintained at 80 psig with nitrogen and the polymerization temperature was 120° C.

Example 2

Characteristics of Fuel used

| Distillation ASTM D-86(°C.) | | | | | CP(°C.) | WAP(°C.) |
|---|---|---|---|---|---|---|
| ibp | 20 | 50 | 90 | $fb_p$ | | |
| 228 | 280 | 310 | 351 | 374 | +5.0 | 0.0 |

An additive combination comprising 250 p.p.m. of each of Additive X, Additives B, C and D was included in the fuel and tested at −14° C. and the fuel was found to pass with a 15 micron screen.

A comparative test using a mixture of 333 p.p.m. of each of additives B, C and D showed the finest mesh the fuel would pass was 35 to 40 microns.

Example 3

Fuel 1 was as described in the previous example and the seven other fuels used had the following characteristics:

| FUEL BLEND | RATIO OF COMPONENTS | | | | Cloud Point (°C.) |
|---|---|---|---|---|---|
| | Kerosene | LCGO | LGO | HGO | |
| 2 | 25 | — | 100 | 20 | −3 |
| 3 | 12.5 | 12.5 | 100 | 20 | −2 |
| 4 | — | 25 | 100 | 20 | −2 |
| 5 | — | — | 100 | 10 | −5 |
| 6 | 85 | — | 100 | 30 | −4 |
| 7 | 42.5 | 42.5 | 100 | 30 | −4 |
| 8 | — | 85 | 100 | 30 | −4 |

| Component Characteristic | Distillation ASTM-D86 | | | | | Cloud Point | Density |
|---|---|---|---|---|---|---|---|
| | ibp | 20 | 50 | 90 | fbp | | |
| Kerosine | 152 | 184 | 200 | 226 | 240 | −53 (freeze point) | 0.793 |
| LCCO* | 143 | 195 | 218 | 256 | 293 | −72 (freeze point) | 0.869 |
| LGO** | 200 | 259 | 282 | 318 | 334 | −8 | 0.847 |
| HGO*** | 1.89 | 349 | 381 | 415 | 438 | +20 | 0.883 |

*Light Cracked Gas Oil
**Light Gas Oil
***Heavy Gas Oil

The Additive combinations used and the Test results are set out in the following Table 1.

TABLE 1

| Additive | D | C | B | X | A2 | A1 | Wax Settlement | 10 um | 15 um | 20 um | 25 um | 35 um | LTFT | VW Filter | 45 um |
|---|---|---|---|---|---|---|---|---|---|---|---|---|---|---|
| Fuel 1 | 250 | 250 | 250 | | | | 100% but Fluffy | 50 s | 150 ml 14.5 s | | | | | | |
| | 250 | 250 | 250 | 250 | | | 50% Light | B | B 20 s | 150 ml 12 s | | | | | |
| | 250 | 250 | | 250 | | | 100% | B | 50 ml 15 s | 150 ml 32 s | 180 ml 41 s | | | | |
| | 250 | 250 | 250 | 250 | | | None | B | B | 36 s 25 s | | | | | |
| | 250 | | 150 | 400 | | 200 | 50% light | 70 ml 20 s | | 11.9 s | | | | | |
| Fuel 2 | 250 | 250 | 250 | | | | 10% thick 25% light | | | B | 30 ml 5.7 s | 120 ml 15.3 s | 30 ml 6.6 s | 4.9 s | B |
| | 250 | 250 | | 250 | | | 100% | | | B | 80 ml 7.6 s | 100 ml 8.1 s | | 6.3 s | |
| | 250 | 250 | 250 | 250 | | | 100% | | B | 70 ml 17 s | 110 ml 22 s | 11.4 s | | | |
| | 250 | | 150 | 400 | | 200 | 50% Light | | B | 150 ml 28 s | 9.4 s | | | | |
| Fuel 3 | 250 | 250 | 250 | | | | 10% thick 25% Light | | | | 100 ml 16 s | 2.6 s | | | B |
| | 250 | 250 | | 250 | | | 100% | | | | 60 ml 85 s | 60 ml 6.9 s | | 6.9 s | |
| | 250 | 250 | 250 | 250 | | | 100% | | B | 100 ml 30 s | 16.4 s | | | | |
| | 250 | | 150 | 400 | | 200 | 50% light | | B | 12.5 s | | | | | |
| Fuel 4 | 250 | 250 | 250 | | | | 20% light | | | B | 80 ml 15 s | 27 s | | | B |
| | 250 | 250 | 250 | 250 | | | 100% | | | B | 50 ml 11 s | 100 ml 20 s | 15 s | | |
| | 250 | 250 | | 250 | | | 100% | | B | 50 ml | 130 ml 11.5 s | 40 s 25 s | | | |
| | 250 | 250 | 250 | 250 | | | 100% | B | | | | | | | |
| | 250 | | 150 | 400 | | 200 | 25% light | B | B | 150 ml 24 s | 10.5 s | | | | |
| Fuel 5 | 250 | 250 | 250 | | | | 10% thick | | | | | | | | B |
| | 250 | 250 | 250 | 250 | | | 25% light | | | | | | | | B |
| | 250 | 250 | | 250 | | | 100% | | | | | | | | B |
| | 250 | 250 | 250 | 250 | | | 100% | | | | | | | 9.6 s | |
| | 250 | | 150 | 400 | | 200 | 100% | | | | | | | 50 ml 15 s | B |
| Fuel 6 | 250 | 250 | 250 | | | | 10% thick 90% clear | | | | | | | | B |
| | 250 | 250 | 250 | 250 | | | 25% light | | | | 50 ml 12.4 s | 100 ml 12.2 s | 7.6 s | | |
| | 250 | 250 | | 250 | | | 100% | | | B | 100 ml 9.6 s | 7.6 s | | | |
| | 250 | 250 | 250 | 250 | | | 100% | 50 ml 9.2 s | 120 ml 19 s | 12.1 s | | | | | |
| | 250 | | 150 | 400 | | 200 | 50% light | 150 ml 35 s | | 7.8 s | | | | | B |
| Fuel 7 | 250 | 250 | 250 | | | | 10% thick 90% clear | | | | | B | B | 6.3 s | |
| | 250 | 250 | 250 | 250 | | | 100% | 27 s 17 s | | | | | | | |
| | 250 | 250 | | 250 | | | 100% | | | | B | 120 ml 12.1 s | 8.1 s | | |
| | 250 | 250 | 250 | 250 | | | 100% | 120 ml 20 s | B | 24 s | | | | | |
| | 250 | | 150 | 400 | | 200 | 100% | 18 s 30 s | | | | | | | |
| Fuel 8 | 250 | 250 | 250 | | | | 100% | 48 s | 8.4 s | | | | | | |
| | 250 | 250 | 250 | 250 | | | 100% | 28 s 19 s | | | | | | | |
| | 250 | 250 | | 250 | | | 100% | B | 100 ml 16 s | 10 s | | | | | |
| | 250 | 250 | 250 | 250 | | | 100% | 100 ml 16 s | 100 ml 18 s | 17 s | | | | | |
| | 250 | | 150 | 400 | | 200 | 100% | 23 s 16 s | | | | | | | |

Note
B = blocked mesh
S = Volume passed in number of seconds
B means filter was blocked
*S = Number of seconds for the specified volume to pass the filter 9.6 s

Example 4

The ability of a Fuel 9 to pass through a diesel vehicle main filter was determined in an apparatus consisting of a typical diesel vehicle main filter mounted in a standard housing in a fuel line; the Bosch Type as used in a 1980 VW Golf diesel passenger car, and a Cummins FF105 as used in the Cummins NTC engine series are appropriate. A reservoir and feed system capable of supplying half a normal fuel tank of fuel linked to a fuel injection pump as used in the VW Golf is used to draw fuel through the filter from the tank at constant flowrate, as in the vehicle. Instruments are provided to measure pressure drop across the filter, the flow rate from the injection pump and the unit temperatures. Receptacles are provided to receive the pumped fuel, both 'injected' fuel and the surplus fuel.

In the test the tank is filled with 19 kilogrammes of fuel and leak tested. When satisfactory, the temperature is stabilised at an air temperature 8° C. above fuel cloud point. The unit is then cooled at 1° C./hour to the desired test temperature, and held for 4 hours for fuel temperature to stabilise. The tank is vigorously shaken to fully disperse the wax present; a sample is taken from the tank and 1 litre of fuel removed through a sample point on the discharge line immediately after the tank and returned to the tank. The pump is then started, with pump rpm set to equate to pump rpm at 110 kph road speed. In the case of the VW Golf, this is 1900 rpm, corresponding to an engine speed of 3800 rpm. Pressure drop across the filter and flow rate of fuel from the injection pump are monitored until fuel is exhausted, typically 30 to 35 minutes.

The key measurements are:

Pressure drop across the main filter—always a paper filter, designed to trap particles of 5–10 microns length in the many layers of paper fibres. Typically, filter papers are either spirally wound or star-shaped around a central core, with the paper about 150–300 microns thick. Maximum pore sizes (or 'gaps between fibres' at one level) are about 100 microns, with the majority of 'gaps' ranging from 1–30 microns.

Wax settlement as measured in the previous Examples

Wax passage through the filter measured by differential scanning calorimetry.

RESULTS

The additive formulations used are set out in Table 2, together with the 'FULL PASSAGE LIMIT' or FPL deduced from the rig results.

'FULL PASSAGE' is defined as a run where the peak pressure drop never rose above 10 kPa. This generally means that more than 90% of the wax in the fuel flowed with the liquid fuel through the filter.

Fuel 9 had the following characteristics:

| Distillation ASTM D-86 (°C.) | | | | | Cloud Point (°C.) | WAP(°C.) |
|---|---|---|---|---|---|---|
| IBP | 20% | 50% | 90% | FBP | | |
| 190 | 246 | 282 | 346 | 374 | +3 | 0 |

It can be seen that by including Y or particularly X into the additive system, substantial benefits in vehicle performance may be obtained.

| Additives (ppm) | | | | | | Wax Settlement % | FPL (°C.) |
|---|---|---|---|---|---|---|---|
| A1 | A2 | C | E | X | Y | | |
| 1000 | — | — | — | — | — | 30 | −9(1) |
| — | 250 | 250 | 250 | — | — | None | −15(3) |
| — | 250 | 250 | 250 | 250 | — | None | −25(2) |
| — | 250 | 250 | 250 | — | 250 | None | −20 |

At −27° C. a failure was brought about by fuel viscosity even though almost 100% of the crystals were passing through the filter

We claim:

1. A wax crystal modifier for distillate fuels boiling in the range of 120° to 500° C. comprising (a) at least one compound represented by the structural formula:

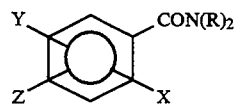

wherein X is selected from the group consisting of —CON(R)$_2$, and —CO$_2^-$ $^+$H$_2$N(R)$_2$; Y and Z are independently selected from the group consisting of —CON(R)$_2$, —CO$_2$R; and R is a C$_{10}$ to about C$_{30}$ alkyl, alkoxyalkyl or polyalkoxyalkyl; (b) at least one comb polymer, and (c) at least one polymer capable of improving the low temperature properties of said fuel selected from compounds of the formula:

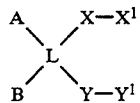

where
A and B may be the same or different and may be alkyl, alkenyl or aryl;
L is selected from the group consisting of
>CH—CH< and
>C=C<
and
A, B and L together can constitute part of a cyclic structure which can be aromatic, alicyclic or mixed aromatic/alicyclic, and with the proviso that the groups —X—X$^1$ and Y—Y$^1$ are located on different carbon atoms constituting L and in that when A, B and L do not constitute part of a cyclic structure one of A or B may be hydrogen and in that when L is non-cyclic ethylenic, said X—X1 and Y—Y1 groupings are present in a cis configuration;
X is selected from the group consisting of —SO$_3$(—), —C(O)—, —C(O)O(—), —R$^4$—C(O)O—, —NR$^3$C(O)—R$^4$O—, —R$^4$OC(O)—, —R$^4$— and —NC(O)—;
X$^1$ is selected from the group consisting of N(+)R$_3^3$R$^1$, N(+)HR$_2^3$R$^1$, H$_2$N(+)R$^3$R$^1$, H$_3$N(+)R$^1$, —NR$^3$R$^1$, and R$^1$;
Y is —SO$_3$(—) or —SO$_2$;
when Y is SO$_3$(—), Y$^1$ is selected from the group consisting of N(+)R$_3^3$R$^2$, HN(+)R$_2^3$R$^2$, H$_2$N(+)R$^3$R$^2$ and H$_3$N(+)R$^2$
and when Y is —SO$_2$—, Y$^1$ is —OR$^2$, —NR$^3$R$^2$ or —R$^2$ and wherein
R$^1$ and R$^2$ are independently selected from the group consisting of alkyl, alkoxy alkyl or polyalkoxyalkyl groups containing at least 10 carbon atoms in their chain;

R$^3$ is hydrocarbyl and each R$^3$ may be the same or different; and

R$^4$ is —(CH$_2$)$_n$ where n is from 0 to 5; polyoxyalkylene esters, ethers, ester/ethers and mixtures thereof; and ethylene-unsaturated ester copolymers.

2. The wax crystal modifier of claim 1 wherein X of (a) is —CON(R)$_2$.

3. The wax crystal modifier of claim 1 wherein X of (a) is —CO$_2^-$ +H$_2$N(R)$_2$.

4. The wax crystal modifier of claim 1 wherein Y and Z of (a) are —CO$_2$R.

5. The wax crystal modifier of claim 1 wherein Y of (a) is —CON(R)$_2$.

6. A wax containing fuel composition comprising a distillate fuels boiling in the range of 120° to 500° C. and (a) a wax crystal modifying amount of at least one compound represented by the structural formula:

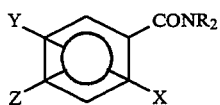

wherein X is selected from the group consisting of —CON(R)$_2$, and —CO$_2^-$ +H$_2$N(R)$_2$; Y and Z are independently selected from the group consisting of —CON(R)$_2$, —CO$_2$R; and R is a C$_{10}$ to about C$_{30}$ alkyl, alkoxyalkyl or polyalkoxyalkyl; and (b) at least one comb polymer, and (c) at least one polymer capable of improving the low temperature properties of said fuel selected from compounds of the formula:

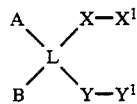

where
A and B may be the same or different and may be alkyl, alkenyl or aryl;
L is selected from the group consisting of
>CH—CH< and
>C=C<
and
A, B and L together can constitute part of a cyclic structure which can be aromatic, alicyclic or mixed aromatic/alicyclic, and with the proviso that the groups —X—X$^1$ and Y—Y$^1$ are located on different carbon atoms constituting L and in that when A, B and L do not constitute part of a cyclic structure one of A or B may be hydrogen and in that when L is non-cyclic ethylenic, said X—X$^1$ and Y—Y$^1$ groupings are present in a cis configuration;
X is selected from the group consisting of SO$_3$(—), —C(O)—, —C(O)O(—), —R$^4$—C(O)O—, —NR$^3$C(O)—R$^4$O—, —R$^4$OC(O)—, —R$^4$— and —NC(O)—;
X$^1$ is selected from the group consisting of N$^{(+)}$R$_3^3$R$^1$, N$^{(+)}$HR$_2^3$R$^1$, H$_2$N$^{(+)}$R$^3$R$^1$, H$_3$N$^{(+)}$R$^1$, —NR$^3$R$^1$, and R$^1$;
Y is —SO$_3$(—) or —SO$_2$;
when Y is SO$_3$(—), Y$^1$ is selected from the group consisting of N$^{(+)}$R$_3^3$R$^2$, HN$^{(+)}$R$_2^3$R$^2$, H$_2$N$^{(+)}$R$^3$R$^2$ and H$_3$N$^{(+)}$R$^2$ and when Y is —SO$_2$—, Y$^1$ is —OR$^2$, —NR$^3$R$^2$ or —R$^2$ and wherein
R$^1$ and R$^2$ are independently selected from the group consisting of alkyl, alkoxy alkyl or polyalkoxyalkyl groups containing at least 10 carbon atoms in their chain;
R$^3$ is hydrocarbyl and each R$^3$ may be the same or different;
and R$^4$ is —(CH$_2$)$_n$ where n is from 0 to 5.; polyoxyalkylene esters, ethers, ester/ethers and mixtures thereof; and ethyleneunsaturated ester copolymers.

7. The composition of claim 6 wherein X of (a) is —CON(R)$_2$.

8. The composition of claim 6 wherein X of (a) is —CO$_2^-$ +H$_2$N(R)$_2$.

9. The composition of claim 6 or 7 wherein Y and Z of (a) are —CO$_2$R.

10. The composition of claim 6 wherein Y of (a) is —CON(R)$_2$.

11. The wax containing fuel composition of claim 6 containing 0.001 to 0.5 wt. % of the wax crystal modifier of (a).

12. An additive concentrate comprising an oil solution containing (a) 5 to 60 wt. % of a compound of the structural formula:

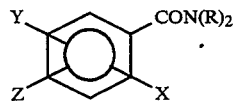

wherein X is selected from the group consisting of —CON(R)$_2$, and —CO$_2^-$ +H$_2$N(R)$_2$; Y and Z are independently selected from the group consisting of —CON(R)$_2$, —CO$_2$R; and R is a C$_{10}$ to about C$_{30}$ alkyl, alkoxyalkyl or polyalkoxyalkyl; (b) at least one comb polymer, and (c) at least one polymer capable of improving the low temperature properties of said fuel selected from compounds of the formula:

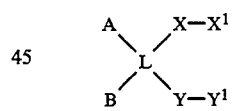

where
A and B may be the same or different and may be alkyl, alkenyl or aryl;
L is selected from the group consisting of
>CH—CH< and
>C=C<
and
A, B and L together can constitute part of a cyclic structure which can be aromatic, alicyclic or mixed aromatic/alicyclic, and with the proviso that the groups —X—X$^1$ and Y—Y$^1$ are located on different carbon atoms constituting L and in that when A, B and L do not constitute part of a cyclic structure one of A or B may be hydrogen and in that when L is non-cyclic ethylenic, said X—X1 and Y—Y1 groupings are present in a cis configuration;
X is selected from the group consisting of SO$_3$(—), —C(O)—, —C(O)O(—), —R$^4$—C(O)O—, —NR$^3$C(O)—R$^4$O—, —R$^4$OC(O)—, —R$^4$— and —NC(O)—;

$X^1$ is selected from the group consisting of $N^{(+)}R_3^3R^1$, $N^{(+)}HR_2^3R^1$, $H_2N^{(+)}R^3R^1$, $H_3N^{(+)}R^1$, $-NR^3R^1$, and $R^1$;

Y is $-SO_3(-)$ or $-SO_2$;

when Y is $SO_3(-)$, $Y^1$ is selected from the group consisting of $N^{(+)}R_3^3R^2$, $HN^{(+)}R_2^3R^2$, $H_2N^{(+)}R^3R^2$ and $H_3N^{(+)}R^2$ and when Y is $-SO_2-$, $Y^1$ is $-OR^2$, $-NR^3R^2$ or $-R^2$ and wherein $R^1$ and $R^2$ are independently selected from the group consisting of alkyl, alkoxy alkyl or polyalkoxyalkyl groups containing at least 10 carbon atoms in their chain;

$R^3$ is hydrocarbyl and each $R^3$ may be the same or different; and $R^4$ is $-(CH_2)_n$ where n is from 0 to 5.;

polyoxyalkylene esters, ethers, ester/ethers and mixtures thereof; and ethylene-unsaturated ester copolymers.

* * * * *